US00RE44543E

(19) United States
(12) Reissued Patent
Rojas et al.

(10) Patent Number: US RE44,543 E
(45) Date of Reissued Patent: Oct. 22, 2013

(54) NAPHTHALENIC COMPOUNDS AS TERMITE BAIT TOXICANTS

(75) Inventors: Maria Guadalupe Rojas, Metairie, LA (US); Juan A. Morales-Ramos, Metairie, LA (US); Frederick Green, III, Madison, WI (US); Thomas A. Kuster, Madison, WI (US)

(73) Assignee: The United States of America as Represented by the Secretary of Agriculture, Washington, DC (US)

(21) Appl. No.: 13/365,452

(22) Filed: Feb. 3, 2012

Related U.S. Patent Documents

Reissue of:

(64) Patent No.: 6,691,453
Issued: Feb. 17, 2004
Appl. No.: 10/135,224
Filed: Apr. 30, 2002

(51) Int. Cl.

| | |
|---|---|
| ***A01N 25/00*** | (2006.01) |
| ***A01N 25/10*** | (2006.01) |
| ***A01N 37/08*** | (2006.01) |
| ***A01N 37/10*** | (2006.01) |
| ***A01N 37/32*** | (2006.01) |
| ***A01N 43/16*** | (2006.01) |
| ***A01N 43/52*** | (2006.01) |
| ***A01N 43/90*** | (2006.01) |
| ***A01N 47/30*** | (2006.01) |
| ***A01N 47/44*** | (2006.01) |
| ***A01N 51/00*** | (2006.01) |

(52) U.S. Cl.
USPC ..... 43/124; 424/84

(58) Field of Classification Search
USPC ..... 43/124; 424/84, 406
See application file for complete search history.

(56) References Cited

U.S. PATENT DOCUMENTS

| | | | | |
|---|---|---|---|---|
| 5,637,298 | A * | 6/1997 | Stowell | 424/84 |
| 6,195,934 | B1 * | 3/2001 | Megargle et al. | 43/131 |
| 6,352,703 | B1 * | 3/2002 | Henderson et al. | 424/406 |

FOREIGN PATENT DOCUMENTS

WO WO 96/32009 * 4/1996

OTHER PUBLICATIONS

"Science Daily"; "Do Termites use "Mothballs" to Ward off Predators?"; printed by American Chemical Society; May 6, 1998.*
USDA TEKTRAN; Nest Fumigation—A Unique Chemical defense strategy of formosan subterranean termites peer reviewed at LA state univ. agri ctr.; Dec. 18, 1998.*
BBC News; Termite 'mothball' keep insects at bay; Apr. 8, 1998.*
Cayman Chemical Company; 6-methoxy naphthalene acetic acid chemical structure; www.caymanchem.com, Apr. 3, 2003.*
Prahl, Scott; Naphthalene; http://omlc.ogi.edu/spectra/photochemCAD/html/naphthalene.html, Apr. 3, 2003.*
Green et al., Protection of Southern Pine from Fungal Decay and Termite Damage with N,N-Napthaloylhydroxylamine. International Biodeterioration & Biodegradation, 39:2-3(1997) 103-111.
Green et al., Inhibition of Wood Decay and Termite Damage by Calcium Precipitation. International Research Group of Wood Preservation, Section 3: Wood Protecting Chemicals, prepared for the 27th Annual meeting in Guadaloupe, French West Indies, May 19-24, 1996.

* cited by examiner

*Primary Examiner* — Kimberly Berona
(74) *Attorney, Agent, or Firm* — John D. Fado; Lesley D. Shaw; Janet I. Stockhausen

(57) ABSTRACT

Termite foods mixed together in a matrix suitable to be used as baits and attractants for termites are provided. They comprise cellulose, naphthalenic compounds, water and potentially other termite-preferred nutrients. Methods of monitoring the presence of termites using such matrices and methods of controlling termites using such matrices to deliver termite toxins are also provided.

11 Claims, No Drawings

NAPHTHALENIC COMPOUNDS AS TERMITE BAIT TOXICANTS

Matter enclosed in heavy brackets [ ] appears in the original patent but forms no part of this reissue specification; matter printed in italics indicates the additions made by reissue.

BACKGROUND OF THE INVENTION

This invention relates to use of naphthalenic compounds as effective bait toxicants for their use in the control of termites.

Damage in the United States attributable to subterranean termites is now estimated to be in excess of one billion dollars a year. All wooden or wood-containing structures are potentially affected, including homes, outbuildings, fences, utility poles, railway sleepers, boats, bridges, retaining walls and even living trees. Since their introduction to the United States within the last half-century, Formosan subterranean termites (FST), Coptotermes formosanus (Shiraki), have become one of the most destructive pests in the contiguous United States. Reasons for this include their massive colonies which can contain tens of millions of individuals, their ability to attack several species of living trees, and their high level of reproduction.

The most successful existing methods for control of subterranean termites are preventive rather than remedial. These include barrier treatments to structures and the pre-emptive treatment of wood materials with chemicals to prevent termite attack. These methods, however, have drawbacks. Physical barriers are not compatible for retrofitting on many existing constructions and may not be completely effective, and chemical treatments are only partially effective and last only about five years.

Low toxicity baits utilizing growth regulators have shown success in reducing damage caused by subterranean termites, with diflubenzuron and hexaflumuron having been particularly effective in suppressing colonies of C. formosanus and Reticulitermes spp. Bait matrices utilized for the baits have consisted of cardboard, filter paper, pine wood, pure cellulose, and recently the use of a nutritionally based matrix. Depending on the species of termite, these matrices have shown to be effective toxicant carriers. Chen et al. (Naphthalene in Formosan Termite Carton Nests; Journal Agricultural Food Chemistry, Vol. 46, No. 6, 1998) disclose the presence of naphthalene in termite carton nests and postulated that it might constitute a unique chemical defense strategy for Formosan termites. Grace et al. (Evaluation of the Termite Resistance of Wood Pressure Treated with Copper Naphthenate; Forest Products Journal, Vol. 43, No. 11/12, November/December 1993) teaches that copper naphthenate is not only toxic to termites but is also highly repellent to them.

While various methodologies and compositions exist for the monitoring and control of termites, there remains a need for the creation of improved tools in this area.

Therefore, it is an object of this invention to provide alternative compounds as bait active ingredients effective as toxicants for termites.

Yet another object is to provide compositions and methods for the effective control of termite populations.

SUMMARY OF THE INVENTION

We have discovered that termites may be more effectively controlled through use of naphthalenic compounds in matrices at fairly low concentrations. These compounds work as an attractant for chemical systems which are toxic to termites. A termite matrix containing nutritionally requisite components enhances its usefulness as a bait and an aggregant for termites. The invention is premised on Applicants' discovery that termites aggregate and feed on food sources that contain naphthalenic compounds.

Termites for which the naphthalene and naphthalene derivatives of this invention are useful include all termite species belonging to the families Rhinotermitidae and Kalotermitidae, preferably Coptotermes formosanus, Reticulitermes flavipes (Kollar) and Reticulitermes virginicus.

The nutritionally based matrix may also be used as a highly effective carrier for enhancing the delivery of these termite toxicants for the purpose of destroying substantial numbers of termites and thus inhibiting termite damage to cellulosic structures such as buildings and trees.

Methods of making termite-preferred matrices of this invention are also provided comprising mixing the various components to form a toxicant containing food.

Methods of killing termites are also provided comprising placing a toxin-containing matrix in a termite habitat upon which the termites will preferentially feed in place of other environmentally-available food sources. The methods preferably also include placing hydrated, water-retaining materials, also referred to herein as water-retention agents, within the termite bait matrix or in the area immediately surrounding the termite matrix to provide a degree of humidity to the immediate area which can be detected by termites to serve as a second means of attracting them.

A termite aggregant comprising a hydrated water-retention agent contained within a termite-accessible container is also provided. The termite-accessible container refers to a container or coating which retains moisture inside but which termites can enter.

DETAILED DESCRIPTION

Naphthalenic compounds incorporated into cellulose-based matrices for the control of termites have been developed. Low concentrations of these chemicals are sufficient to kill native and Formosan termites colonies in field conditions. Naphthalenic compounds are considered to be any of those that possess a base structure of naphthalene. These chemicals can be used in baiting systems as a novel approach to reduce the amount of toxins required to kill termites. The matrix composition comprises cellulose, water, and naphthalene derivatives and termite-preferred nutrients.

The cellulose may be supplied by means of any cellulose-containing material, preferably having at least 50% to greater than 95% cellulose, so long as it does not include chemicals which are repellant to termites. Such usable materials include commercially available cellulose, wood, paper, and cardboard, and are preferably in particulate form for ease of mixing with the other ingredients of the matrix. Sawdust may be used from any plant source but is preferably from woods preferred by termites such as aspen, sitka spruce, maple, birch, sweet gum and related woods or any such species possessing a low content of feeding deterrent chemicals as determinable by means well known in the art. Alternate sources of sawdust, while usable, may contain chemicals in amounts that reduce the utility of such sawdust materials due to either repellant or toxic effects.

The degree to which the presence of a particular component causes termites to prefer a food over other foods not containing the component, or containing greater or lesser amounts thereof, may readily be assessed using methods known in the art.

The matrix further comprises naphthalenic compounds present in amounts ranging from about 10 ppm to about 500 ppm. Usable compounds are seen to include N-hydroxynaphthalimide (NHA), 1,8-napthalimide and sodium, magnesium, potassium and calcium salts thereof and copper naphthenate and zinc naphthenate.

Subterranean termites prefer moist foods. To be more attractive than other available foods in the environment, the formulation of this invention should be preferably moist. Enough water should be used to allow mixing of the matrix material, and/or completely hydrate the particulate or solid cellulose materials and to provide excess water to maintain a humid environment. In general about three-fourths by weight of the matrix should be water, but this may vary with the water content ranging from about 20% to about 90% by weight of the composition.

A water-retention agent capable of absorbing water and releasing it slowly to the environment can be used to ensure an acceptable moisture level in the matrix material as well as to serve as another means for termite aggregation. Examples of such materials include agar and polyacrylamide, but may include any substance not otherwise possessing a repellant effect. Examples of preferred usable materials include the polyacrylamide graft copolymer such as Terrawet® T-400 Aquawet (Terrawet Company, San Diego, Calif.), which can absorb and retain up to a thousand times their own weight in water. These materials should be hydrated, preferably fully-hydrated, with the addition of at least thirty times their weight in water containing the water-soluble naphthalene derivatives, such as NHA. The hydrated water-retaining materials may be mixed with the matrix.

The inventors have discovered that termites are attracted during their foraging to high humidity conditions, preferably at least about 80% humidity, and more preferably at least about 90% humidity. Thus, moisture-retaining material as described above is preferably placed in the immediate environment of the bait matrix to provide a humidity readily detectable by, and attractive to, termites. In a preferred embodiment in which a polyacrylamide graft copolymer such as Terrawet® 400 Aquawet is used as the water-retaining agent, it may be placed in the area of a termite bait or monitoring station at an application rate effective for eliciting an aggregant response, that is, from about 1 g to about 10 g (dry weight) per square foot. The hydrated-polyacrylamide, preferably hydrated to a NHA-water: polymer weight ratio of at least about 30:1, with a final concentration of NHA of 900 ppm, can be injected into the soil around the bait station by pressure using commercially available injectors, preferably to a radius around the bait matrix of at least about 2.5 cm, or placing it on the base of the station or inside of the above ground station or in the cracks of walls and trees or other locations susceptible to termite infestation. Other water-retaining agents as described above can alternatively be used, adjusting ratios to achieve 80% to 90% humidity as will be readily apparent to those skilled in the art. The bait container is made from a material such as paraffin, beeswax, polyurethane foam, styrofoam and fibrous casing tubes.

Naphthalenic compounds may be used to retard extreme deterioration of wood interceptors and to congregate termites to its immediate environment for purposes of monitoring the size and presence of termite populations, e.g., by observing termites and counting or otherwise estimating the number of termites present by measuring the consumption of wood interceptors. Typical monitoring strategies utilize approximately one bait station per 10-15 linear feet. The significantly faster response of termites to treated pine wood as compared to untreated pine wood results in enhanced monitoring efficacy. Additionally, these chemicals may be used alone or in combination with active secondary toxicants used in bait matrices such as streptomycin sulfate, rifampicin, albendazole, neomycin sulfate, sorbic acid, antimycotics, benzofenyl ureas, imidacloprid, hydroximethanon, juvenile hormone mimics and used in combination with preferred wood such as maple, sitka spruce, birch, douglas fir, red gum, yellow poplar, white pine or yellow pine wood to extend the period of termite activity at the monitoring site.

The matrix materials of this invention, may be encased in materials or containers which are water-retentive such that they substantially prevent evaporation of the moisture in the food, but which are vapor-permeable to a degree sufficient to allow termites to detect odors coming from the matrices.

EXAMPLES

Example 1

NHA-sodium Salt

For bait matrices with a final concentrations of NHA sodium salt of either 250 ppm or 500 ppm, the following procedure was used. A total of 25 mg or 50 mg, respectively of the NHA sodium salt was weighed using a Mettler balance. The NHA sodium salt complex was placed into a 50 ml sterile screw cap conical tube (#62.547.004; Sarstedt, Newton, N.C.) and dissolved with 40 ml nutritive solution described in Example 2 of U.S. patent application Ser. No. 09/294,499 filed Apr. 20, 1999, hereby incorporated by reference. Under a laminar flow hood, this product was mixed with 27 ml more of sterile nutritional supplement in a 250 ml sterile glass bottle (prepared as reported by M. G. Rojas and J. A. Morales-Ramos, April 2001, "Bait matrix for delivery of chitin synthesis inhibitors to the Formosan subterranean termite [Isoptera: Rhinotermitidae]," J. Econ. Entomol. 94(2) :506-510) hereby incorporated by reference. The bottle was tightly closed with a screw cap and manually shaken for 2 minutes. The mixture was added to 33 g of sterile cellulose as reported by Rojas and Morales-Ramos (2001) supra. The mixture was manually homogenized using a stainless steel spatula. To encase the bait matrix, tubes made of fibrous casing material (#124B; L.E.M. Products, Inc., Miamitown, Ohio) were cut into 150 mm long portions as reported by Rojas and Morales-Ramos (2001) supra. Fifty grams of bait matrix containing NHA sodium salt was compacted into one end of the inlet tube, and the open end and of the inlet tube was closed with a rubber band. The bait casing was placed inside of the foraging box adjacent to a 10 g piece of pine wood, taking care that it was partially covered with sand. Control bait matrix was prepared minus NHA, and presented in the same way as the treatment matrix to Formosan termites taken from three different colonies, with two boxes per locality totaling six boxes of 2500 termites per treatment. (Rojas and Morales-Ramos [2001] supra). All the experimental boxes were maintained under dark conditions at 27±1° C., and 90±2% relative humidity. Observations were done every 72 hours until all the termites died. The time to reach 100% mortality was measured and recorded. Mean comparisons among treatments and control were conducted.

TABLE 1

Colonies of 2500 termite workers alive after 1, 2 and 2½ months of feeding on non repellent lethal concentrations of NHA sodium

| NHA-sodium salt[a] | 1 Month Colonies Alive | 2 Months Colonies Alive | 2½ Months Colonies Alive |
|---|---|---|---|
| 0 (Control) | 6 | 6 | 6 |
| 250 | 4 | 3 | 0 |
| 500 | 3 | 1 | 0 |

[a]Concentration in parts per million.

Table 1 shows that all termites in the experimental colony containing NHA were dead in about 2½ months while the termites in the control boxes were still alive after 6 months. The cuticle of the dead termites from the treatment boxes had a yellowish color with a rubbery consistency. At a concentration of NHA >500 ppm, the acceptability of the bait is reduced, since some termite colonies required more than 8 hours to start feeding on it. This chemical agent acts very strongly against the termites, producing a mortality of a 2,500-worker colony in about 3 weeks, depending on the health and age of the colony. At NHA concentrations above 10,000 ppm, the bait becomes unpalatable and consumption is almost non existent above 20,000 ppm. The preferred dose is 500 mg of NHA per kilogram of bait matrix.

Example 2

N-hydroxynaphthyalimide Sodium Salt

N-hydroxynaphthyalimide (NHA) which is commercially available as pure chemical, is dissolved in distilled water using a sterile container; At concentrations of 500 ppm, NHA is effective as bait active ingredient taking a mean time to kill C. formosanus in 2½ months in lab conditions. Concentrations greater than 500 and up to 1500 ppm, are also effective but mean killing times are not significantly different. N-hydroxynaphthyalimide (NHA) sodium salt 99% (Product No. A16027, CAS No. 6207-89-2), obtained from Avocado Research Chemicals Ltd. (Massachusetts) was separately incorporated into a bait matrix (ARS bait matrix) as described in U.S. patent application Ser. No. 09/294,499 filed Apr. 20, 1999, hereby incorporated by reference. Note Example 1, above, for the creation of the NHA salt. The bait matrix was prepared by weighing 1.25 g lecithin (USB #18240), 0.450 g ergoesterol (Sigma #E-6510), 3.75 g ethyl alcohol (Quantum MT #194A31) and 650 g drinking water (Barbe's Dairy, West Wego, La.) into a 1 L glass bottle and mixing well using a glass bar. The opening of the bottle was covered with a foam stopper, the bottle cap was loosely placed on top of the stopper, and the stopper covered with foil. After autoclaving for 20 minute at 120° C., the bottle was closed tightly and allowed to cool down. 350 g cellulose powder (Bio-Serv #3425) was weighed into a 3 L stainless steel bowl. Polyacrylamide copolymer was weighed into a second 1 L glass beaker, distilled water was added and the beaker was tightly covered with foil. After autoclaving, the bottle was closed tightly and allowed to cool. The beakers were tightly covered with foil and sterilized by autoclaving at 120° C. for 20 minutes.

Under a laminar flow hood, yeast hydrolysate (ICN Biomed. #103304) was added to the lecithin-containing mixture using a sterile spatula and the mixture was shaken until the yeast hydrolysate was incorporated. The bottle was tightly closed.

Using a sterile spatula, the lecithin-containing mixture was added to the cellulose and mixed well. Finally, the polyacrylamide copolymer was added to the mixture and homogenized. The beaker was covered with foil and plastic to avoid contamination and loss of water. The mixture was compacted and divided into pieces of about 25-125 g each at concentrations of 50, 250, and 500 ppm respectively. The bioassay was run using the protocol of Example 1. Preliminary results testing a dose range of NHA sodium salt from 50, 250, and 500 ppm had shown that 500 ppm was sufficient to induce formosan termite mortality within about two months without any signs of repellence to the termites. Repellence was observed at NHA sodium salt doses higher than 1500 ppm.

Example 3

Field Evaluation

Underground Exterra bait stations (Ensystex, Fayetteville, N.C.) were placed according to manufacturer directions around 20 houses in a heavily Reticulitermes spp. infested neighborhood surrounded by mainly pine forest in Past Christian, Miss. The stations were placed, approximately 20 feet apart and 5 feet away from the outside wall of the house. Monthly inspections were conducted to determine termite activity. Once termites were found in the station, 150 g of the ARS bait matrix (see Example 2) containing 250 ppm NHA was placed in the station for the first year of the experiment. The dose was increased in the second year to 500 ppm because of the constant movement of termites from the forest area to the stations. The bait matrix-NHA was prepared as above and exposed to the termites contained in the Exterra bait station, consecutively monthly inspections were conducted and bait matrix-NHA was added as required. Data on bait consumption, temperature of the soil and time to kill the colony was recorded. Reticulitermes flavipes were very abundant in the study site. The distribution of the infestation was in patches. For the typical infested house, termites were found in 3 of 6 stations. For this type of environmental setting, 600 g of bait matrix which is equivalent to 240 mg of NHA was required to kill the colony. It took about 9 months (from September-May) for the bait matrix to show its effectiveness which was evaluated by the presence of dead termites on the surface of the bait matrix container and interceptors. Table 2 shows termite activity and bait consumption from different baitings done in Past Christian, Mississippi. The length of time we believe was due to the size of the colony as well as the lack of feeding during winter in which termite feeding activity is greatly reduced.

TABLE 2

Termite activity and bait consumption in a field test in Past Christian, Mississippi

| | Active Stations | | Bait (Cum. weight in g) | |
|---|---|---|---|---|
| Date | Number | Percentage* | Added | Consumed** |
| 09/26 | 22 | 95.7 | 2,700 | 0.0 |
| 10/27 | 10 | 43.5 | 3,600 | 600 |
| 11/20 | 10 | 41.7 | 4,650 | 1,200 |
| 12/18 | 8 | 33.3 | 4,950 | 1,500 |
| 01/29 | 6 | 24.0 | 5,100 | 1,500 |
| 02/26 | 12 | 50.0 | 5,550 | 1,500 |
| 03/27 | 13 | 56.5 | 6,450 | 1,500 |
| 05/01 | 16 | 55.2 | 7,650 | 3,150 |
| 05/29 | 11 | 36.7 | 8,400 | 3,750 |
| 06/26 | 16 | 50.0 | 9,450 | 4,800 |

TABLE 2-continued

Termite activity and bait consumption in a field test in Past Christian, Mississippi

| | Active Stations | | Bait (Cum. weight in g) | |
|---|---|---|---|---|
| Date | Number | Percentage* | Added | Consumed** |
| 07/31 | 12 | 33.3 | 10,800 | 6,000 |
| 08/28 | 17 | 47.2 | 12,000 | 7,200 |
| 09/25 | 21 | 52.5 | 13,950 | 7,950 |
| 11/02 | 18 | 42.9 | 15,900 | 10,800 |
| 11/27 | 13 | 28.9 | 17,250 | 11,250 |
| 12/29 | 13 | 28.9 | 17,850 | 11,850 |
| 01/29 | 11 | 24.4 | 17,850 | 11,850 |
| 02/26 | 15 | 33.3 | 18,750 | 12,600 |

*Calculated as the percent stations that are active from the cumulative number of stations that have been active to the monitoring day.
**Calculated from fully consumed bait bags.

Example 4

NHA-sodium Salt in Wooden Interceptors

NHA as a wood preservative has been extensively studied (F. Green III, T. A. Kuster, L. Ferge, and T. L. Highley, 1997. Protection of southern pine from fungal decay and termite damage with N,N-Naphthaloylhydroxylamine. Inter. Biodeter. and Biodeg. 39(2-3):103-111; D. M. Crawford and F. Green III, 1999. Protection of southern pine using N,N-Naphthaloylhydroxylamine: Field tests, soft-rot cellars and aquatic bioassay leach testing. Internat. Res. Group on Wood Preserv. Doc. No: IRG/WP 99-30204). Monitoring termite activity in baiting systems is conducted by the use of wooden interceptors constructed from out of aspen, southern yellow pine, white or yellow poplar. In humid environments such as the Southeastern United States, a problem with degradations of such interceptors by fungi frequently occurs. We have noticed that low concentrations of NHA from 200 to 1000 ppm is acceptable to retard fungal growth without presenting any deleterious effect in the termites when incorporated into wooden materials. For bait efficacy, when the chemical is impregnated on pieces of wood the concentration that is retained varies as well as the efficacy. The interceptors are preferably pressure treated (S. T. Lebow and S. A. Halverson, 1999. Effect of prestain on the treatability of western hemlock with chromated copper arsenate. Res-Note FPL-RN-0269. Madison, Wis.: USDA, Forest Service, Forest Products Laboratory 5p.) with aqueous solutions of 0.2-1000 ppm of NHA (F. Green III, et al., 1997, supra and D. M. Crawford et al., supra).

Pieces of aspen wood (20×3.5×0.5 cm) were pressure treated with NHA as described above in Lebow and Halverson, supra and placed into 6 underground Exterra bait stations installed next to Formosan subterranean termite infested trees in New Orleans. The stations also contained pieces of untreated aspen wood as control. Inspections were done biweekly and pieces damaged by termites were replaced. After field testing 75 to 1000 ppm is acceptable and 500 ppm being the optimal. When applied on wood instead of the matrix, the NHA dose varies with the impregnation properties of each wood species.

Example 5

Copper Naphthenate Laboratory Study

Copper naphthenate (Product No. PS-2028, Chem Service, West Chester, Pa.) was dissolved in 90% warm ethanol at 3 different concentrations of 50, 100 and 200 ppm. The ethanol solution was mixed with the liquid part of the ARS bait matrix (see Example 2) and bait was prepared and presented to the termites as above in Example 1 having 4 repetitions per dose and a control. It was observed that at 50 ppm of chemical, all termites in 50% of the boxes died at about 8 weeks; and termites in 75% of the boxes died at about 10 weeks; at 100 ppm all termites died in the boxes at 8 weeks, and at 200 ppm all termites died in all tested boxes at 8 weeks. All termites in the treatments were dead by week 12. A great variability in acceptance of the bait and time to kill was observed at the 200 ppm dose. The results are reported in Table 3.

TABLE 3

Percent colonies of 2500 termite workers alive after 8, 10, and 12 weeks of feeding on non repellent lethal concentrations of copper naphthenate

| | Time After Treatment (wks) | | |
|---|---|---|---|
| Copper naphthenate[a] | 8 | 10 | 12 |
| 0 (Control) | 100 | 100 | 100 |
| 50 | 50 | 25 | 0 |
| 100 | 0 | 0 | 0 |
| 200 | 0 | 0 | 0 |

[a]Concentration in parts per million.

It is understood that the foregoing detailed description is given merely by way of illustration and that modifications and variations may be made therein without departing from the spirit and scope of the invention. For example, choice of specific components and their relative proportions in the matrices or wood material may readily be determined by those skilled in the art without undue experimentation using the teachings hereof.

What is claimed is:

1. A termite bait matrix comprising:

a) cellulose;

b) water; and c) one or more naphthalenic compounds selected from the group consisting of N-hydroxynaphthalimide and sodium, magnesium, potassium and calcium salts thereof, 1,8-napthalimide, copper naphthenate and zinc naphthenate in amounts [sufficient in termite matrices to kill termites] *ranging from about 10 ppm to about 500 ppm*.

2. The termite bait matrix of claim 1 further comprising a water-retention agent.

3. The termite bait matrix of claim 2 wherein the water-retention agent is in an amount up to about 0.05 g/kg.

4. The termite bait matrix of claim 1 further comprising a termite toxicant.

5. The termite matrix of claim 4 wherein said termite toxicant is selected from the group consisting of:

streptomycin sulfate, rifampicin, albendazole, neomycin sulfate, sorbic acid, antimycotics, benzofenyl ureas, imidacloprid, hydroximethanon, juvenile hormone mimics.

6. The termite bait matrix of claim 1 contained within a termite-accessible container or coating.

7. A method of killing termites comprising:

a) placing the termite bait matrix of claim 1 in a termite habitat; and b) allowing termites to feed on said bait matrix.

8. A method of monitoring termite activity in a region comprising:

a) placing the termite bait matrix of claim 1 in said region; and b) assessing the presence of termites at the site of said termite bait matrix.

9. The method of claim 8 wherein said termite bait matrix further comprises a water-retention agent.

10. The method of claim 9 wherein said termite bait matrix is contained within a water-retentive, vapor-permeable coating or container.

*11. The termite bait matrix of claim 1 wherein the one or more naphthalenic compounds selected from the group consisting of N-hydroxynaphthalimide and sodium, magnesium, potassium and calcium salts thereof, 1,8-napthalimide, copper naphthenate and zinc naphthenate in amounts ranging from about 10 ppm to about 500 ppm.*

* * * * *